United States Patent [19]

Ikeda et al.

[11] 4,331,824
[45] May 25, 1982

[54] PROCESS FOR PREPARATION OF HIGH PURITY ISOBUTYLENE

[75] Inventors: Minoru Ikeda, Hiroshima; Teruhiko Yoshioka; Kazutaka Inoue, both of Otake, all of Japan

[73] Assignee: Mitsubishi Rayon Co., Ltd., Tokyo, Japan

[21] Appl. No.: 166,681

[22] Filed: Jul. 7, 1980

[30] Foreign Application Priority Data

Jul. 16, 1979 [JP] Japan .................................. 54-90036

[51] Int. Cl.³ .............................................. C07C 1/20
[52] U.S. Cl. .................................... 585/638; 585/639
[58] Field of Search ................................ 585/639, 638

[56] References Cited

U.S. PATENT DOCUMENTS 3,510,538  5/1970  Rosenthal ........................... 585/639
4,011,272  3/1977  Matsuzawa et al. ................ 585/638
4,178,317  12/1979  Horn et al. .......................... 585/638
4,232,177  11/1980  Smith ................................... 585/639

Primary Examiner—Curtis R. Davis
Attorney, Agent, or Firm—Cushman, Darby & Cushman

[57] ABSTRACT

Highly purified isobutylene, up to 99.9% pure, is obtained by treating a reaction mixture such as that recovered from an isobutylene-containing hydrocarbon mixture also containing an aqueous solution of an aliphatic carboxylic acid having 1 to 6 carbon atoms that has been reacted in an acidic ion exchanger and from which the unreacted hydrocarbons have been removed. The operative ingredients of the treated mixture are tertiary butyl alcohol, secondary butyl alcohol and their esters of the carboxylic acid employed. When treated with an acidic ion exchanger the carboxylic acid is first formed which inhibits the secondary butyl alcohol and secondary butyl ester of the acid from decomposing and high purity isobutylene is recovered therefrom by conventional distillation.

7 Claims, 2 Drawing Figures

PROCESS FOR PREPARATION OF HIGH PURITY ISOBUTYLENE

SCOPE OF THE INVENTION

The present invention provides a process in which high purity isobutylene having a purity of at least 99.9% is prepared in a high yield at a high productivity and a low cost.

BACKGROUND OF THE INVENTION

There are various starting materials for the preparation of isobutylene including the residue (hereinafter referred to as "spent BB") left after extraction of butadiene from a BB fraction (butene-butadiene fraction) obtained as a by-product at cracking of naptha. Also, there is an isobutylene-containing hydrocarbon mixture such as a decomposition gas formed by fluidized catalytic decomposition of light oil (kerosine). However, in each of these starting materials, normal butene isomers and butanes having a boiling point close to that of isobutylene are also present with the isobutylene. Thus from a cost of effectiveness viewpoint, separation of isobutylene by customary distillation is difficult. Thus in the industrial process customarily used in this art, the characteristic property of isobutylene, that is a higher reactivity as compared with the reactivity of other butenes, is utilized, and an isobutylene-containing hydrocarbon mixture is contacted with, for example, a 50 to 70% by weight aqueous solution of sulfuric acid to selectively extract isobutylene.

As is well recognized in the art, this process is defective in that special materials are needed to fabricate the equipment used because sulfuric acid is employed. Further, undesirable oligomers of isobutylene, such as a dimer, are formed in large quantities. In addition, the purity of isobutylene obtained according to this process is 97 to 98%, and in order to increase the purity to 99.9% or more, additional operations such as separation using a molecular sieve and another sulfuric acid absorption should be carried out, resulting in increased manufacturing costs.

Considerable attention has been given in this process in order to eliminate these defects. The main object of these studies is to isolate a reaction solvent or catalyst that provides a higher reactivity with isobutylene and a lower reactivity with other butenes, in other words, a reaction solvent or catalyst having a high selectivity to isobutylene and providing a high productivity so as to fully utilize the difference of isobutylene over other butenes in respect to their relative reactivities.

In order to improve the purity of the isobutylene final product, it is one of the important requirements that the selectivity of the reaction system should be high. Furthermore, in order to obtain high purity isobutylene it is important to use a heterogeneous catalyst, which allows easy separation of the catalyst from the reaction product, as the catalyst for reaction of isobutylene. More specifically, an unreacted hydrocarbon mixture is contained more or less in a liquid reaction mixture obtained by the reaction of isobutylene, and if this unreacted hydrocarbon mixture is not separated from the reaction product of isobutylene, it is incorporated into isobutylene when isobutylene is obtained by the decomposition of the reaction product of isobutylene, resulting in a reduction of the purity. When a catalyst is present at the step of separating the reaction product of isobutylene from this unreacted hydrocarbon mixture, the reaction product of isobutylene is decomposed, and even if high productivity and high yield are both attained in the reaction, both the productivity and yield are reduced by this decomposition and good results are not obtained. Accordingly, a heterogeneous catalyst such as an ion exchange resin is preferred as the catalyst for reaction of isobutylene.

A process for the preparation of isobutylene, based on the above-mentioned concept, is disclosed in, for example, U.S. Pat. No. 3,026,362. This process comprises separating isobutylene in the form of a carboxylic acid ester from a hydrocarbon mixture in the presence of a saturated aliphatic carboxylic acid having 1 to 4 carbon atoms by using an acidic ion exchange resin having a macro-reticular structure as the catalyst, and decomposing the ester by using as the catalyst the same acidic ion exchange resin. In this method, the carboxylic acid ester is formed in a high yield at a high productivity, but the difference of isobutylene as opposed to normal butenes in respect to the reactivity is not sufficient. For example, when isobutylene in spent BB is reacted with acetic acid and is converted to tertiary butyl acetate according to this process, secondary butyl acetate is formed as a by-product in an amount of about 1%. Accordingly, if the reaction product is decomposed, the purity of the resulting isobutylene is about 99%.

Another process has also been proposed in which isobutylene is hydrated in a hydrocarbon mixture by using a solvent and a catalyst and separating isobutylene in the form of tertiary butyl alcohol. Whatever solvent and catalyst may be used in this process, however, the tertiary butyl alcohol so formed contains a considerable amount of secondary butyl alcohol which is undesirable as it is not suitable for production of high purity isobutylene. Accordingly, in order to obtain high purity isobutylene, there should be adopted a method for dehydration of tertiary butyl alcohol, as disclosed in, for example, Soviet Union Pat. No. 202,881, in which tertiary butyl alcohol is separated from secondary butyl alcohol by fine distillation utilizing a slight difference of the volatility between tertiary butyl alcohol and secondary butyl alcohol. Thereafter, the thus separated tertiary butyl alcohol is dehydrated and decomposed.

The present applicants have studied such reactions with a view to developing a cost effective process capable of producing high purity isobutylene having a purity of at least 99.9% with economical advantages, and as the result, we have found that high purity isobutylene can be prepared when a reaction gas obtained by treating a mixture containing tertiary butyl alcohol and a tertiary butyl ester of an aliphatic carboxylic acid having 1 to 6 carbon atoms with an acidic ion exchanger is subjected to customary distillation separation.

The mixture of tertiary butyl alcohol and tertiary butyl ester as described above is obtained according to a method disclosed in, for example, U.S. Pat. No. 4,011,272, the disclosure of which is hereby incorporated by reference. More specifically, an isobutylene-containing hydrocarbon mixture and an aqueous solution of an aliphatic carboxylic acid having 1 to 6 carbon atoms are reacted in the presence of an acidic ion exchanger. The unreacted hydrocarbons are separated from the reaction mixture by distillation to form a residual reaction mixture liquid (I). Then, a mixture (II) containing tertiary butyl alcohol and a tertiary butyl ester of the carboxylic acid is obtained together with a portion of water from liquid (I) by conventional distillation.

According to this procedure, we obtained mixture (II), and the content of secondary butyl alcohol, which is a by-product, and secondary butyl ester of the carboxylic acid, which is also a by-product, in the mixture (II) were determined with improved analysis accuracy. It was found that the secondary butyl alcohol and the secondary butyl ester of the carboxylic acid were together present in a total amount of 0.3 mol%. This means that even though the hydration conditions disclosed in U.S. Pat. No. 4,011,272 provides a good selectivity with respect to isobutylene, the purity of isobutylene that can be expected according to this process is about 99.7%. In order to further improve the purity, one should use a special method of removal of secondary butyl alcohol and secondary butyl ester of the carboxylic acid by fine distillation.

BRIEF SUMMARY OF THE INVENTION

We have now found that when the above-mentioned mixture is treated with an acidic ion exchanger, decomposition of the tertiary butyl ester of the carboxylic acid occurs first and by the action of the carboxylic acid formed by this decomposition, the secondary butyl alcohol and the secondary butyl ester of the carboxylic acid are inhibited from decomposing. The result is that high purity isobutylene having a purity of at least 99.9% can be obtained by subjecting the decomposition gas to ordinary distillation.

DETAILED DESCRIPTION OF THE INVENTION

Figure 1:
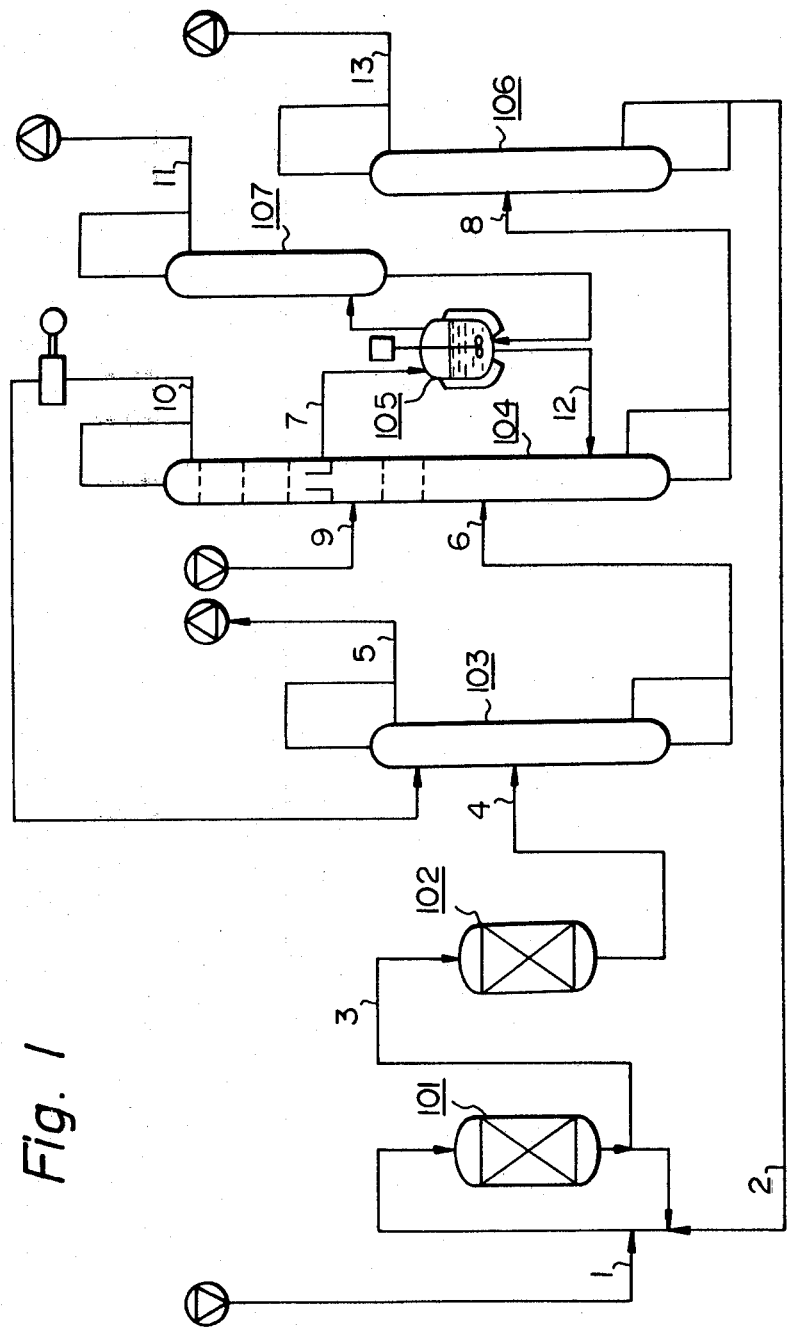
FIGS. 1 and 2 are schematic flow charts of different embodiments of the invention in which high purity isobutylene is obtained.

With reference to experimental results, we will now specify the characteristics of the above-mentioned mixture (II) that may be subjected to decomposition with an acidic ion exchange resin and thus are suitable for production of high purity isobutylene according to our process.

A flask equipped with a stirrer and a reflux cooler was charged with 30 cc of a commercially available, strongly acidic ion exchange resin (the H type; exchange capacity =1.7 mg equivalent/ml), and either 50 g of a liquid A (free of a carboxylic acid) more fully identified in Table 1, or 56 g of a liquid B (containing a carboxylic acid) more fully identified in Table 1 was charged into the flask. The flask was positioned into a thermostatically controlled tank to maintain the contents at a temperature of 80° C. and the reaction product gas was analyzed at predetermined intervals to obtain the results shown in Table 2.

As will be apparent from the results shown in Table 2, in the decomposition of a mixture of tertiary butyl alcohol and a tertiary butyl ester of a carboxylic acid, decomposition of the secondary butyl alcohol and the secondary butyl ester of the carboxylic acid is inhibited by the presence of the carboxylic acid, (in this case acetic acid) formed by decomposition of the tertiary butyl ester. This decomposition system, therefore, is suitable for production of high purity isobutylene according to the process of our invention.

TABLE 1

| Liquid | Composition (% by weight) | | | | |
|---|---|---|---|---|---|
| | Tertiary Butyl Alcohol | Secondary Butyl Alcohol | Secondary Butyl Alcohol | Water | Acetic Acid |
| Liquid A | 80 | 7 | 3 | 10 | 0 |
| Liquid B | 71.4 | 6.25 | 2.68 | 8.93 | 10.7 |

TABLE 2

| | Normal Butene Concentration (ppm) in Reaction Product Gas | | | | Decomposition Ratio of TBOH at a Reaction Time of 370 Minutes |
|---|---|---|---|---|---|
| | Reaction Time | | | | |
| | 60 Minutes | 160 Minutes | 260 Minutes | 370 Minutes | |
| Liquid A | 40 | 230 | 600 | 1550 | 82.5% |
| Liquid B | 30 | 140 | 330 | 920 | 77.6% |

As will readily be understood from the above experimental results, according to a preferred embodiment of the process of the present invention, the catalyst used for advancing the decomposition reaction, and specifically an acidic ion exchanger, is present in the place where the carboxylic acid is present. In order to separate isobutylene formed by the decomposition reaction from tertiary butyl alcohol, water and carboxylic acid present in the reaction system, a distillation column should be used. If the acidic ion exchanger is present in the bottom portion of this distillation column, the decomposition reaction is advanced in the presence of the carboxylic acid and high purity isobutylene can be advantageously prepared according to our process.

Investigations were made to determine preferred decomposition reaction conditions, and it was found that the preferred reaction temperature is in the range of from about 60 to about 120° C. If the reaction temperature is lower than 60° C., the rate of decomposition of tertiary butanol was low, and if the reaction temperature is higher than 120° C., decomposition of secondary butanol becomes vigorous and good results can not be obtained, and furthermore, the decomposition catalyst is then required to be heat resistant. A lower reaction pressure is preferred because the rate of the decomposition reaction is high, but since the boiling point of distilled isobutylene under atmospheric pressure is −6° C., a low reaction pressure is disadvantageous from the economical viewpoint because a special cooling medium should be used. And since an aqueous solution of tertiary butanol was the property that the aqueous solution freezes at about 0° C., if the reaction pressure is too low clogging is readily caused in the interior of the distillation column, resulting in reduction of the operation stability. If the reaction pressure is atmospheric pressure, therefore, it is preferred to carry out a batchwise operation or a distillation operation under elevated pressure if the process was continuous. Accordingly, it is preferred to use a reaction pressure of from atmospheric pressure to about 4.5 Kg/cm$^2$ G, under which cooling water of a re-cooling column can be used.

An example of an application of the process of the present invention will now be described. It is known in the art that tertiary butyl alcohol has recently been used as the starting material for synthesis of methacrolein by gas phase catalytic oxidation.

A most effective utilization of the process of the present invention is in simultaneous production of such tertiary butyl alcohol and high purity isobutylene. According to this embodiment, a residual reaction mixture liquid (I), obtained by reacting an isobutylene-containing hydrocarbon mixture with an aqueous solution of an aliphatic carboxylic acid having 1 to 6 carbon atoms in the presence of an acidic ion exchanger and removing the unreacted hydrocarbon mixture from the resulting liquid reaction product, is subjected to extraction distillation using water as the extracting agent to recover the carboxylic acid ester of tertiary butyl alcohol in the form of a mixture (III) with water and part of tertiary butyl alcohol. The mixture (III) then is treated in the presence of the acidic ion exchanger and isobutylene is recovered by distillation, whereby high purity isobutylene can be prepared. Separately, tertiary butyl alcohol is recovered by distillation from the residual liquid left after separation of the mixture (III) from the above-mentioned residual reaction mixture (I). Thus, high purity isobutylene and tertiary butyl alcohol can be simultaneously prepared according to this embodiment of the process of the present invention. The main components of the residual reaction mixture (I) are tertiary butyl alcohol, the carboxylic acid ester of tertiary butyl alcohol, water and the carboxylic acid together with minor amounts of secondary butyl alcohol and the carboxylic acid ester of secondary butyl alcohol.

If this residual reaction mixture liquid (I) is supplied to an intermediate stage of a distillation column and an extractive distillation is carried out while supplying water into the distillation column from the head thereof. The carboxylic acid ester of tertiary butyl alcohol is separated on the distillate side. This is described in U.S. patent application Ser. No. 91,246 filed Nov. 2, 1979, the disclosure of which is hereby incorporated by reference. The distillate contains parts of tertiary butyl alcohol, secondary butyl alcohol and the carboxylic acid ester of secondary butyl alcohol in addition to the carboxylic acid ester of tertiary butyl alcohol. In short, the distillate is the above-mentioned mixture (III). The ratio of the carboxylic acid ester of tertiary butyl alcohol to tertiary butyl alcohol in this mixture (III) is higher than this ratio in the residual reaction mixture liquid (I), because the carboxylic acid ester is concentrated.

Both of tertiary butyl alcohol and the carboxylic acid ester of tertiary butyl alcohol can form isobutylene when they are contacted and treated with an acidic ion exchange resin, but the decomposition rate of the carboxylic acid ester is much higher than that of tertiary butyl alcohol. Accordingly, if mixture (III) is partially decomposed to selectively decompose the carboxylic acid ester of tertiary butyl alcohol, carboxylic acid is formed, and therefore, the difference of the decomposition rate between this decomposition and the decomposition of secondary butyl alcohol and the carboxylic acid ester of secondary butyl alcohol is further increased over the decomposition rate difference in the whole decomposition of the mixture (II). As the result the purity of isobutylene is remarkably improved.

The concentration of the residual carboxylic acid ester of tertiary butyl alcohol in the liquid obtained by this partial decomposition is much lower than the carboxylic acid ester concentration attained by the hydrolysis process disclosed in U.S. patent application Ser. No. 91,246, filed Nov. 2, 1979. Thus, the decomposition ratio of the carboxylic acid ester can be enhanced.

This indicates that when the liquid formed by the above-described partial decomposition is combined with the liquid left after distillation separation of mixture (III) and tertiary butyl alcohol is separated from the resulting mixture by distillation, the concentration of the carboxylic acid ester, the main impurity in tertiary butyl alcohol, can be reduced to a level lower than the carboxylic acid ester concentration in the process of U.S. patent application Ser. No. 91,246, filed Nov. 2, 1979. Accordingly, the purity of tertiary butyl alcohol is substantially improved and the amount used of the carboxylic acid is reduced, with the result that economical advantages are increased. According to this embodiment of the present invention which is directed to simultaneous preparation of high purity isobutylene and tertiary butyl alcohol, additional highly desirable results can be thus attained also in connection with the preparation of tertiary butyl alcohol.

One instance of the above embodiment of the process according to the present invention in which high purity isobutylene and tertiary butyl alcohol are simultaneously prepared from an isobutylene-containing hydrocarbon mixture will now be described with reference to FIG. 1.

DETAILED DESCRIPTION OF THE DRAWINGS

In FIG. 1, reference numerals 101 and 102 represent first and second hydration vessels packed with an acidic ion exchanger. An isobutylene-containing hydrocarbon mixture is supplied to the first hydration vessel from line 1 and an aqueous solution of a carboxylic acid is supplied to the first hydration vessel from line 2. It is preferred that the operation be carried out under conditions such that an effluent from the first hydration vessel (line 3) is homogeneous. An effluent from the second hydration vessel 102 is supplied to a hydrocarbon-separating distillation column 103 through line 4, and an unreacted isobutylene-containing hydrocarbon mixture is taken out of distillation column via line 5. Line 6 is positioned to feed the residual reaction mixture liquid (I) from the distillation column 103.

Reference numeral 104 represents an extractive distillation column for spearating tertiary butyl alcohol and the carboxylic acid ester of tertiary butyl alcohol from the liquid fed via line 6, and water is supplied to this column through line 9. Line 7 is a conduit positioned to remove the carboxylic acid ester in the form of the mixture (III) with a portion of butyl alcohol and water. The top portion of 104 functions as a distillation column and line 7 is disposed to sufficiently reduce the content of the hydrocarbon mixture dissolved in the mixture (III). The hydrocarbon mixture separated in this distillation column is returned to the distillation column 103 through the line 7 by means of a compressor (shown schematically).

The mixture (III) taken out from line 7 is fed to a decomposition vessel 105 packed with an acidic ion exchanger, where decomposition occurs primarily on the carboxylic acid ester and isobutylene is formed. The decomposition gas resulting from the reaction is taken from vessel 105 and treated in distillation column 107 while high purity isobutylene is taken out through line 11. The partially decomposed liquid, which is obtained as a residue after decomposition of almost of all carboxylic acid ester, is taken from vessel 105 via line 12 and fed to an appropriate stage of the recovery zone of the above-described extractive distillation column 104 or to line 8. The bottom liquid of the extractive distillation column 104 is fed to a tertiary butyl alcohol-separating distillation column 106 through the line 8. The aqueous solution of the carboxylic acid is taken out through line 2. According to the above-mentioned flow chart, high purity isobutylene and tertiary butyl alcohol can be simultaneously prepared.

Figure 2:
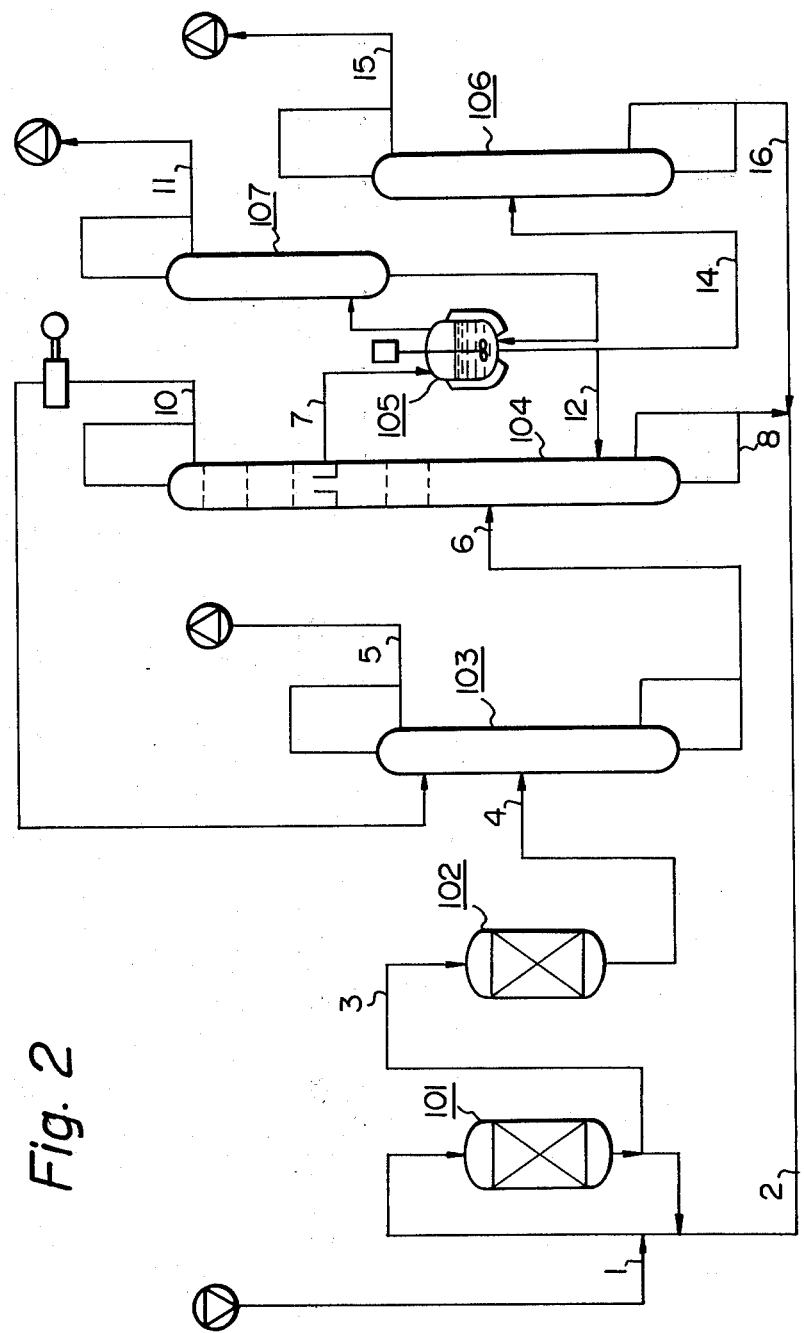

One instance of the embodiment of the process of the present invention in which high purity isobutylene is prepared from an isobutylene-containing hydrocarbon mixture is illustrated in FIG. 2. In this figure, the flow to the line 6 is the same as shown in FIG. 1. Reference numeral 104 represents an ordinary distillation column provided with a side stream. Tertiary butyl alcohol and carboxylic acid ester are not left in the line 8, but rather the aqueous solution of the carboxylic acid is taken out via line 8, returned to the hydration vessel through the line 2 and used again. The mixture (II) removed from column 104 via line 7 is decomposed in a decomposition vessel 105 packed with an acidic ion exchanger, isobutylene is separated by distillation in the distillation column 107 and high purity isobutylene is removed through line 11.

The aqueous solution of carboxylic acid, the other decomposition product, is taken out through line 12 and fed to the recovery zone of the distillation column 104 to recover unreacted tertiary butyl alcohol and the like, and then the aqueous solution of the carboxylic acid is returned to the hydration vessel through line 2 and used again. Secondary butyl alcohol and the carboxylic acid ester of secondary butyl alcohol, which have not been substantially decomposed in the decomposition vessel, are fed to the distillation column 106 together with the aqueous solution of the carboxylic acid which is the main decomposition product through line 14 while a part of the liquid is removed through line 12 and returned to distillation column 104. In the distillation column 106, the liquid is separated into the aqueous solution of small amount of tertiary butyl alcohol, secondary alcohol and its ester and an aqueous carboxylic acid solution. The aqueous solution of the carboxylic acid is returned to the hydration vessel through line 16 and the aqueous solution of small amount of tertiary butyl alcohol, secondary alcohol and its ester is withdrawn from the systems through line 15. The amount of this solution withdrawn is a minute amount corresponding to the sum of the amounts of secondary butyl alcohol and its carboxylic acid ester formed by the hydration reation. According to this procedure, good results can be continuously obtained.

EXAMPLE 1

This Example illustrates the simultaneous preparation of high purity isobutylene and tertiary butyl alcohol according to the flow chart of FIG. 1. The composition of the hdyrocarbon mixture used as the starting material is shown in Table 3.

Starting material was supplied at a rate of 100 mols per hour from line 1 and an aqueous solution of acetic acid having an acetic acid/water molar ratio of 1:2 was supplied at a rate of 176 mols per hour from line 2. The first and second hydration vessels were packed with 7 l and 6 l of a sulfonic acid-type cation exchange resin, respectively. The reaction temperature in the first hydration vessel was 77° C. and the reaction temperature in the second hydration vessel was 70° C., and the reaction pressure was 10 Kg/cm$^2$G.

An ordinary sieve tray plate column was used as the hydrocarbon-separating column 103. The composition of the liquid removed from the top of the column 103 via line 5 is shown in Table 3. The composition of the bottom liquid (line 6) is shown in Table 4. From these results, it was found that the conversion of isobutylene was 92% and the selectivity for tertiary butyl acetate was 4.4%. The amount of the dimer of isobutylene formed as the by-product was only a trace, and by improved accuracy analysis, it was confirmed that the total molar amount of secondary butyl alcohol and secondary butyl acetate was 0.3 mol% based on the amount of isobutylene reacted.

The distillation column 104 for concentration of tertiary butyl acetate had 40 stages in total and the upper 5 stages were arranged for separating the hydrocarbon mixture dissolved in the reaction liquid as the vent gas while recycling all of the condensate. Tertiary butyl acetate is taken out through line 7 in the form of a liquid mixture (II) together with tertiary butyl alcohol and water from the tray of the fifth stage counting from the top. The composition of the mixture in the line 7 is shown in Table 4. The amount of this distillate was 43 mols per hour.

Deionized water was supplied at a rate of 0.97 Kg per hour to the tray of the sixth stage counting from the top. The decomposition vessel 105 was a jacketed stirring tank in which was suspended 3.5 l of a sulfonic acid-type ion exchange resin having an exchange capacity of 2.0 mg equivalent/ml and diameter of about 0.5 mm. The decomposition vessel 105 was operated at a temperature of 90° C. under a pressure of 2 Kg/cm$^2$G. The decomposition gas from the decomposition vessel was supplied to the bottom of the sieve tray distillation column 107 having 5 stages. The composition of high purity isobutylene obtained from line 11 is shown in Table 4.

The purity was 99.97%. The yield of isobutylene was 26% of the amount of isobutylene reacted at the hydration step, and the remainder of reacted isobutylene was substantially converted to tertiary butyl alcohol. The composition of the effluent (line 12) from the decomposition vessel is shown in Table 4. The decomposition ratio of tertiary butyl acetate in the decomposition vessel was 98%, and the decomposition ratio of tertiary butyl alcohol was 48%. The content of tertiary butyl acetate in tertiary butyl alcohol recovered from the line 13 was 0.074 mol% which, for comparison, is less than ½ of the tertiary butyl acetate content attained in published U.S. patent application Ser. No. 91,246, filed Nov. 2, 1979, that is, 0.17 mol%.

TABLE 3

| Components | Line 1 | Line 5 |
| --- | --- | --- |
| isobutylene | 45.0 mol % | 6.1 mol % |
| 1-butene | 26.0 mol % | 44.4 mol % |
| 2-butene | 15.0 mol % | 25.6 mol % |
| butane | 14.0 mol % | 23.9 mol % |

TABLE 4

| Components | Line 6 | Line 7 | Line 11 | Line 12 | Line 13 |
| --- | --- | --- | --- | --- | --- |
| isobutylene | 0.06 mol % | — | 99.97 mol % | — | — |
| n-butene | 0.69 mol % | 0.002 mol % | 75 ppm | — | — |
| butane | 0.24 mol % | — | 25 ppm | — | — |
| tertiary butyl alcohol | 22.3 mol % | 43.9 mol % | — | 22.8 mol % | 56.4 mol % |
| tertiary butyl acetate | 1.02 mol % | 4.18 mol % | — | 0.08 mol % | 0.074 mol % |

TABLE 4-continued

| Components | Line 6 | Line 7 | Line 11 | Line 12 | Line 13 |
|---|---|---|---|---|---|
| secondary butyl alcohol | 0.037 mol % | 0.037 mol % | — | 0.05 mol % | 0.13 mol % |
| secondary butyl acetate | 0.020 mol % | 0.026 mol % | — | 0.01 mol % | 0.055 mol % |
| acetic acid | 32.0 mol % | 0.028 mol % | — | 4.1 mol % | — |
| water | 43.7 mol % | 51.8 mol % | 200 ppm | 73.0 mol % | 43.3 mol % |

EXAMPLE 2

According to the flow chart shown in FIG. 2, the residual reaction mixture liquid (I) (line 6) was obtained by the hydration reaction and the separation of hydrocarbons in the same manner as described in Example 1. The liquid (I) was supplied to the distillation column 104 having 25 stages in total. Minute amounts of hydrocarbons in the line 6 were separated in the upper five stages of column 104, and tertiary butyl alcohol, the carboxylic acid ester of tertiary butyl alcohol and a part of water were taken out through the line 7 in the form of the liquid mixture (II) from the tray of the fifth stage counting from the top. The composition of the mixture (II) in the line 7 is shown in Table 5. The aqueous carboxylic acid solution was taken out from the bottom of column 104 through line 8. The composition of the aqueous solution in the line 8 is shown in Table 5. The mixture (II) was supplied to the decomposition vessel 105. The decomposition vessel 105 was a jacketed stirring tank in which was suspended 13 l of a sulfonic acid-type ion exchange resin having an ion-exchange capacity of 1.8 mg equivalent/ml and diameter of about 0.5 mm. Decomposition vessel 105 was operated at a temperature of 90° C. under a pressure of 1.5 Kg/cm$^2$G. The decomposition gas from the decomposition vessel was supplied to the bottom of a sieve tray distillation column 107 having 5 stages. The purity of isobutylene recovered through the line 11 was 99.96%.

The liquid residue in the decomposition vessel was discharged through line 12. By analysis of the composition of this residue, it was found that the decomposition ratio of tertiary butyl alcohol was 91% and the decomposition ratio of tertiary butyl acetate was 99%. The STY (space time yield) value of isobutylene was 3.1 mol/l hr.

The liquid in the line 12 was taken out in an amount corresponding to 10% of the flow rate from the line 14 and fed to another distillation column 106, where residual tertiary butyl alcohol, secondary butyl alcohol and their esters of acetic acid were separated. The aqueous solution of acetic acid from the column 106 was recycled through the line 16 and used again for the dehydration reaction. The remainder of the liquid in line 12 was supplied to the recovery zone of distillation column 104.

Acetic acid and water were added to the liquid in the line 8, and the mixture was returned to the hydration vessel and used again.

The compositions of the liquids in this Example are shown in Table 5.

TABLE 5

| Components | Line 6 | Line 7 | Line 8 | Line 11 | Line 12 |
|---|---|---|---|---|---|
| isobutylene | 0.06 mol % | — | — | 99.96 mol % | — |
| n-butene | 0.69 mol % | 0.002 mol % | — | 200 ppm | — |
| butane | 0.24 mol % | — | — | 25 ppm | — |
| tertiary butyl alcohol | 22.3 mol % | 45.1 mol % | — | — | 4.14 mol % |
| tertiary butyl acetate | 1.02 mol % | 1.92 mol % | — | — | 0.020 mol % |
| secondary butyl alcohol | 0.037 mol % | 0.84 mol % | — | — | 0.84 mol % |
| secondary butyl acetate | 0.020 mol % | 0.21 mol % | — | — | 0.21 mol % |
| acetic acid | 32.0 mol % | 0.02 mol % | 35.2 mol % | — | 1.90 mol % |
| water | 43.7 mol % | 51.9 mol % | 64.8 mol % | 200 ppm | 92.9 mol % |

EXAMPLE 3

This example illustrates an embodiment of the invention in which a mixture of tertiary butyl alcohol, tertiary butyl acetate and water, prepared in the same manner as described in Example 1 (corresponding to the liquid in the line 7 in Example 1), is treated under atmospheric pressure in a batchwise reaction vessel to synthesize high purity isobutylene.

In a 3-liter capacity glass flask connected to a distillation column having an inner diameter of 25 mm and including 10 stages, 1 l of a commercially available, sulfonic acidic ion exchange resin (the H type; exchange capacity =1.7 mg equivalent/ml, diameter of about 0.5 mm) was packed, and 1140 g of a mixture shown in Table 6 was charged in the flask and heated by an oil bath under agitation. The inner temperature of the flask was maintained at 68° C. for 1.5 hours and the liquid in the flask was sampled. Then, the inner temperature of the flask was elevated to 72° C. and this temperature was maintained for 2.5 hours. During this period, the distillation column was operated at the reflux ratio of 2. The operation pressure was atmospheric pressure.

If the operation was conducted so that deviation of the amount of the distillate was avoided, freezing was not caused in the distillation column. The purity of isobutylene thus obtained was 99.96%. The composition of the residual liquid was analyzed at the intermediate point of the reaction and at the point of termination of the reaction to obtain results shown in Table 6, from which it is seen that the rate of decomposition of tertiary butyl acetate was high.

TABLE 6

| Components | Starting Mixture | Composition of Residual Liquid after 1.5 Hours Reaction and Conversions | Composition of Residual Liquid after 4.0 Hours Reaction and Conversions |
|---|---|---|---|
| tertiary butyl alcohol | 42.8 mol % | 37.3 mol % | 19.6 mol % |

TABLE 6-continued

| Components | Starting Mixture | Composition of Residual Liquid after 1.5 Hours Reaction and Conversions | Composition of Residual Liquid after 4.0 Hours Reaction and Conversions |
|---|---|---|---|
| tertiary butyl acetate | 5.73 mol % | 0.22 mol % | 0.048 mol % |
| secondary butyl alcohol | 0.035 mol % | 0.034 mol % | 0.037 mol % |
| secondary butyl acetate | 0.022 mol % | 0.021 mol % | 0.011 mol % |
| water | 51.4 mol % | 56.9 mol % | 74.6 mol % |
| acetic acid | 0.027 mol % | 5.56 mol % | 5.71 mol % |
| conversion of tertiary butyl alcohol | | 12.8% | 54.2% |
| conversion of tertiary butyl acetate | | 96.2% | 99.2% |

We claim:

1. A process for the preparation of high purity isobutylene comprising treating a mixture of tertiary butyl alcohol and a tertiary butyl ester of an aliphatic carboxylic acid having 1 to 6 carbon atoms in the presence of an acidic ion exchanger and separating isobutylene in a highly purified form by distillation.

2. A process for the preparation of isobutylene according to claim 1, wherein during the treatment in the presence of the acidic ion exchanger at least a part of the tertiary butyl alcohol in the mixture is not decomposed but remains as such in the mixture.

3. A process for the preparation of isobutylene according to claim 1 or 2, the mixture is treated in the presence of the acidic ion exchanger at a temperature of about 60 to about 120° C. under a pressure in the range of from atmospheric pressure to about 4.5 Kg/cm²G.

4. A process for the preparation of isobutylene according to claim 1, 2 or 3, wherein the acidic ion exchanger is positioned in the bottom portion of a distillation column for distilling and refining isobutylene formed by decomposition of said mixture.

5. A process for the preparation of isobutylene according to claim 1, wherein the mixture treated is a mixture of tertiary butyl alcohol and a tertiary butyl ester of an aliphatic carboxylic acid having 1 to 6 carbon atoms recovered from a liquid reaction mixture obtained by subjecting an isobutylene-containing hydrocarbon mixture to hydration reaction with an aqueous solution of an aliphatic carboxylic acid having 1 to 6 carbon atoms in the presence of an acidic ion exchanger.

6. A process for the preparation of isobutylene according to claim 1, 2, 3, 4 or 5, wherein the purity of the isobutylene product is at least 99.9%.

7. A process for preparing isobutylene at a purity of at least 99.9% consisting of:
  (i) treating an aqueous mixture of tertiary butyl alcohol and a tertiary butyl ester of a $C_1$-$C_4$ carboxylic acid with an acid ion exchanger at a temperature in the range of about 60° C. to about 120° C. at a pressure from atmospheric to about 4.5 Kg/cm² G to produce an isobutylene-rich reaction gas; and
  (2) distilling the thus obtained reaction gas and recovering high purity isobutylene therefrom.

* * * * *